(12) United States Patent  
Hoffa (10) Patent No.: US 8,554,309 B2  
(45) Date of Patent: Oct. 8, 2013

(54) LOCALIZING OBTURATOR WITH SITE MARKING CAPABILITY

(75) Inventor: Michael Hoffa, Brownsburg, IN (US)

(73) Assignee: Hologic, Inc., Marlborough, MA (US)

( * ) Notice: Subject to any disclaimer, the term of this patent is extended or adjusted under 35 U.S.C. 154(b) by 349 days.

(21) Appl. No.: 12/888,641

(22) Filed: Sep. 23, 2010

(65) Prior Publication Data

US 2012/0078086 A1   Mar. 29, 2012

(51) Int. Cl.
*A61B 5/00* (2006.01)

(52) U.S. Cl.
USPC ........................................................ 600/431

(58) Field of Classification Search
USPC ........... 600/414, 420, 426, 431; 606/116, 117
See application file for complete search history.

(56) References Cited

U.S. PATENT DOCUMENTS

| | | | |
|---|---|---|---|
| 7,651,505 B2 * | 1/2010 | Lubock et al. | 606/116 |
| 7,761,137 B2 * | 7/2010 | Hardin et al. | 600/431 |
| 7,783,336 B2 * | 8/2010 | Macfarlane et al. | 600/407 |
| 7,877,133 B2 * | 1/2011 | Burbank et al. | 600/431 |
| 8,377,032 B2 * | 2/2013 | Bates | 604/506 |

* cited by examiner

*Primary Examiner* — Max Hindenburg
(74) *Attorney, Agent, or Firm* — Vista IP Law Group LLP (57) ABSTRACT

A target localizing and marking device is provided including a cannula having proximal and distal ends and a lumen therebetween, and a tip member releasably attached to the distal end, where the tip member includes and outer shell and at least one inner chamber. The device further includes at least one image enhancing component disposed on the outer shell and/or within the at least one inner chamber, at least one marking component disposed in the at least one inner chamber, and a tip member deployment mechanism. The deployment mechanism has a manually engageable actuator, a portion of which is dimensioned to slidably pass through the lumen of the cannula, and is operable to separate the tip member from the cannula and deploy the tip member to a predetermined target site. In some implementations, the device is magnetic resonance imaging (MRI) compatible and is identifiable under MRI.

11 Claims, 11 Drawing Sheets

LOCALIZING OBTURATOR WITH SITE MARKING CAPABILITY

FIELD OF THE INVENTION

The present invention relates to the field of medical devices and, more particularly, to a magnetic resonance imaging (MRI) compatible obturator capable of localizing and selectively marking a target site, such as a breast biopsy site.

BACKGROUND OF THE INVENTION

Medical procedures have advanced to stages where less invasive or minimally invasive surgeries, diagnostic procedures and exploratory procedures have become desired and demanded by patients, physicians, and various medical industry administrators. To meet these demands, improved medical devices and instrumentation have been developed, such as medical grade cannulas, introducers, localization obturators, marker deployment devices, vacuum assisted biopsy devices, and other endoscopic related devices.

In the field of tissue biopsy, minimally invasive biopsy devices have been developed that require only a single insertion point into a patient's body to remove one or more tissue samples. One such biopsy device incorporates a "tube-within-a-tube" design that includes an outer piercing needle having a sharpened distal end and a lateral opening that defines a tissue receiving port. An inner cutting member is slidingly received within the outer piercing needle, which serves to excise tissue that has prolapsed into the tissue receiving port. A vacuum is used to draw the excised tissue into the tissue receiving port and aspirates the excised tissue from the biopsy site once severed.

Among other features, such biopsy devices are generally designed for use in conjunction with Magnetic Resonance Imaging (MRI). This compatibility is realized because many of the components of the biopsy devices are made of materials that do not interfere with the MRI equipment or are otherwise compatible therewith. It is often desirable to perform biopsies in conjunction with MRI because it is a non-invasive visualization modality capable of defining the margins of a tumor. During such procedures, a localizing obturator is often used to assist the physician in identifying the precise location of the biopsy site to ensure that the biopsy device and other medical treatments are accurately placed within the biopsy site. Hence, it is critical that a portion of the obturator be clearly identifiable under MRI so that the physician can clearly identify the biopsy site before performing a biopsy procedure.

Regardless of the method or instrument used to perform the biopsy, after the biopsy is completed, subsequent examination of the surgical site may be necessary, either in a follow up examination or for treatment of a cancerous lesion. Therefore, a separate marker deployment instrument must be employed to release and insert a site marker into the biopsy site for future identification.

SUMMARY

According to one aspect, the present invention is directed to a medical target localizing and marking device. The device includes a cannula defining a proximal end, a distal end and a lumen extending between the proximal and distal ends, and a tip member releasably attached to the distal end of the cannula, where the tip member defines and outer shell and at least one inner chamber. The device further includes at least one image enhancing component disposed on the outer shell of the tip member and/or within the at least one inner chamber, at least one marking component disposed in the at least one inner chamber, and a tip member deployment mechanism. The deployment mechanism has a manually engageable actuator, a portion of which is dimensioned to slidably pass through the lumen of the cannula, and is operable to separate the tip member from the distal end of the cannula and deploy the tip member to a predetermined target site. In some aspects, the target localizing and marking device is magnetic resonance imaging (MRI) compatible.

In some embodiments, the deployment mechanism includes a push rod slidably disposed within the cannula and movable between a retracted position and an extended position. The push rod is generally biased toward the retracted position and is adapted to contact the tip member in the extended position to separate the tip member from the cannula and deploy the tip member to the predetermined target site.

In some embodiments, the cannula includes at least one retaining member adapted to secure the tip member to the cannula when the push rod is in the retracted position, and release the tip member when the push rod is in the extended position. In some such embodiments, the at least one retaining member is a holding tab connected to an internal surface of the lumen of the cannula adjacent to the distal end of said cannula. The holding tab serves to frictionally engage at least a portion of the tip member, while the push rod serves to overcome the frictional engagement to deploy the tip member.

In some embodiments, the tip member and image enhancing component are bioabsorbable. Further, in some embodiments, the marking component is a solid component detectable under multiple imaging modalities. And in some such embodiments, the predetermined shape is one of a venus symbol, bow-tie, and ribbon.

In some embodiments, the imaging enhancing component is compatible with magnetic resonance imaging (MRI) and detectable under MRI. And in some such embodiments, the image enhancing component is at least one of a metallic material and a liquid contrast agent.

Figure 4A:
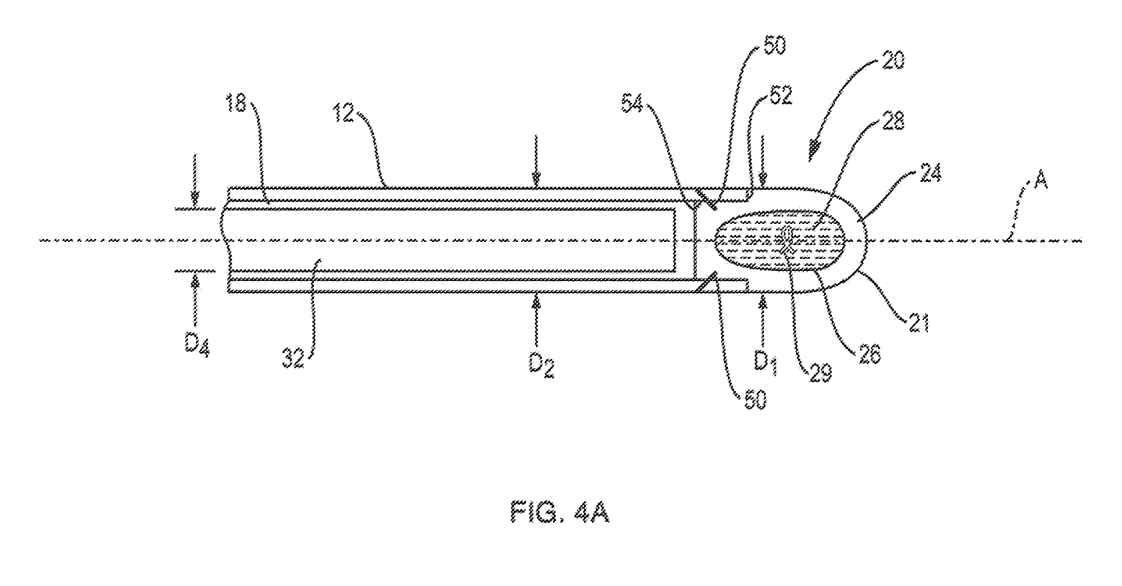
FIG. 4A is a partial side cross-sectional view of the distal end of the device shown in FIG. 1.
Figure 4B:
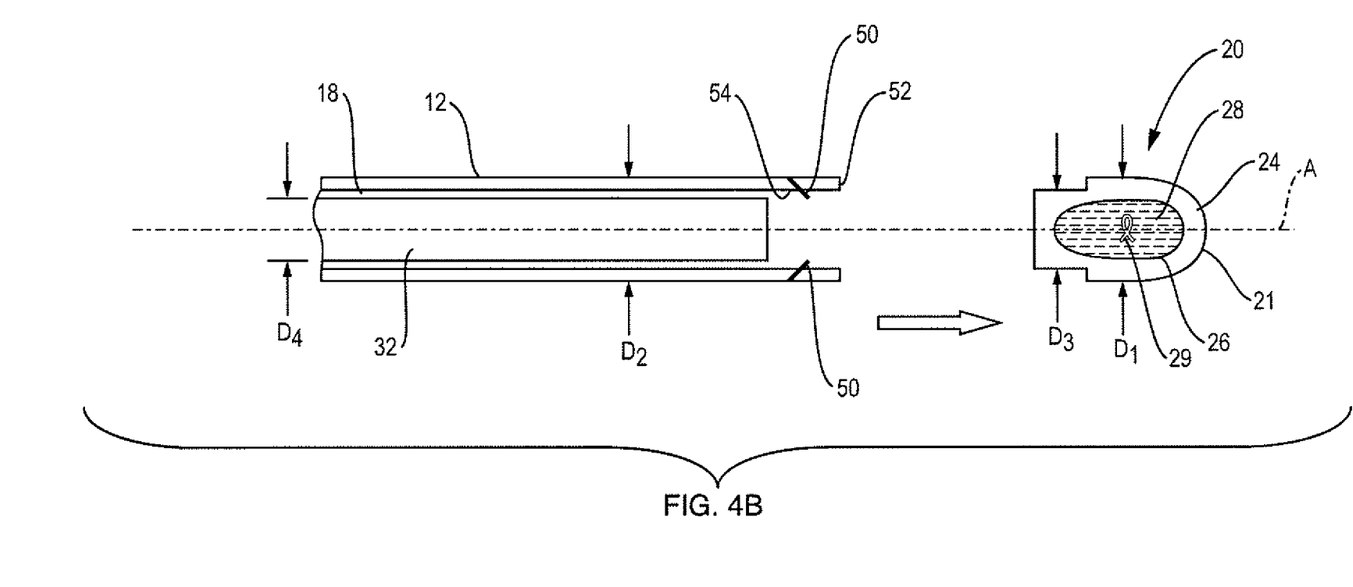
FIG. 4B is a partial side cross-sectional view of the distal end of the device shown in FIG. 2.
Figure 4C:
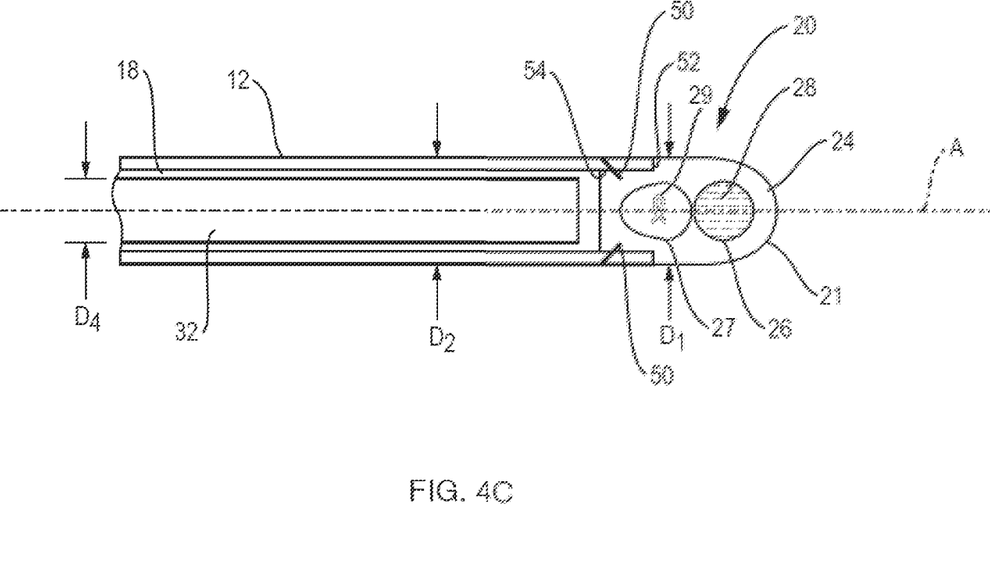
FIG. 4C is a partial side cross-sectional view of the distal end of a target localizing and marking device according to another embodiment of the invention.

In some embodiments, the tip member 20 defines a single inner chamber 26 and both the image enhancing component 28 and the marking component 29 are housed in the single chamber 26 (FIG. 4A), or the tip member 20 defines two chambers 26, 27 and the image enhancing component 28 is housed in one 26 of the two chambers and the marking component 29 is housed in the other 27 of the two chambers (FIG. 4C).

According to a second aspect, the invention is directed to a biopsy system. The system includes an introducer cannula insertable into a patient's tissue, which includes an open proximal end, an open distal end and a lumen extending between the proximal and distal ends; an introducer stylet selectively insertable within the lumen of the introducer cannula and configured for tissue penetration; and a separate target localizing and marking device that is selectively insertable within the lumen of the introducer cannula. The target localizing and marking device includes a cannula defining a proximal end, a distal end and a lumen extending between the proximal and distal ends, and a tip member releasably attached to the distal end of the cannula and defining and outer shell and at least one inner chamber.

The device further includes at least one image enhancing component disposed on the outer shell of the tip member and/or in the at least one inner chamber, at least one marking component disposed in the at least one inner chamber, and a tip member deployment mechanism. The deployment mechanism has a manually engageable actuator, a portion of which is dimensioned to slidably pass through the lumen of the cannula, and is operable to separate the tip member from the distal end of the cannula and deploy the tip member to a predetermined target site. The system further includes a separate biopsy device having an outer cannula selectively insertable within the lumen of the introducer cannula and defining an at least one tissue receiving aperture, and a cutting cannula slidably disposed over or within the outer cannula. The cutting cannula includes a cutting edge for severing tissue residing in the at least one tissue receiving aperture. In some aspects, the system is magnetic resonance imaging (MRI) compatible.

According to another aspect, the invention is directed to medical procedure. The procedure comprises the steps of inserting a target localizing and marking device into a patient's body to a predetermined target site. The device includes a cannula defining a distal end, a tip member releasably attached to the distal end of the cannula and including at least one image enhancing component and at least one marking component, and a tip member deployment mechanism. The deployment mechanism has a manually engageable actuator and is operable to separate the tip member from the distal end of the device cannula and deploy the tip member to a predetermined target site.

The procedure further comprises the steps of confirming the location of the target site relative to the target localizing and marking device by identifying at least one of the image enhancing component and marking component via a predetermined imaging modality; actuating the deployment mechanism; and marking the target site post-biopsy by releasing the tip member from the device cannula and deploying the tip member into the target site. In some aspects of the procedure, the imaging modality is magnetic resonance imaging (MRI).

In some embodiments, after confirming the location of the target site relative to the target localizing and marking device, the procedure further includes the steps of removing the target localizing and marking device from the patient's body; inserting a biopsy device into the patient's body and harvesting a tissue sample with the biopsy device; removing the biopsy device from the patient's body; and reinserting the target localizing and marking device into the patient's body.

Further, in some embodiments, prior to inserting the target localizing and marking device, the procedure further includes the steps of inserting an introducer stylet into a patient's body and creating a pathway through the patient's tissue leading to a predetermined target site through which the target localizing and marking device passes.

Details of one or more implementations of the invention are set forth in the accompanying drawings and in the description below. Further features, aspects, and advantages of the invention will become apparent from the description, the drawings, and the claims.

Although the drawings represent embodiments of the present invention, the drawings are not necessarily to scale and certain features may be exaggerated in order to better illustrate and explain the present invention. The exemplification set out herein illustrates certain embodiments of the invention, in one, or more forms, and such exemplifications are not to be construed as limiting the scope of the invention in any manner.

DETAILED DESCRIPTION

Figure 1:
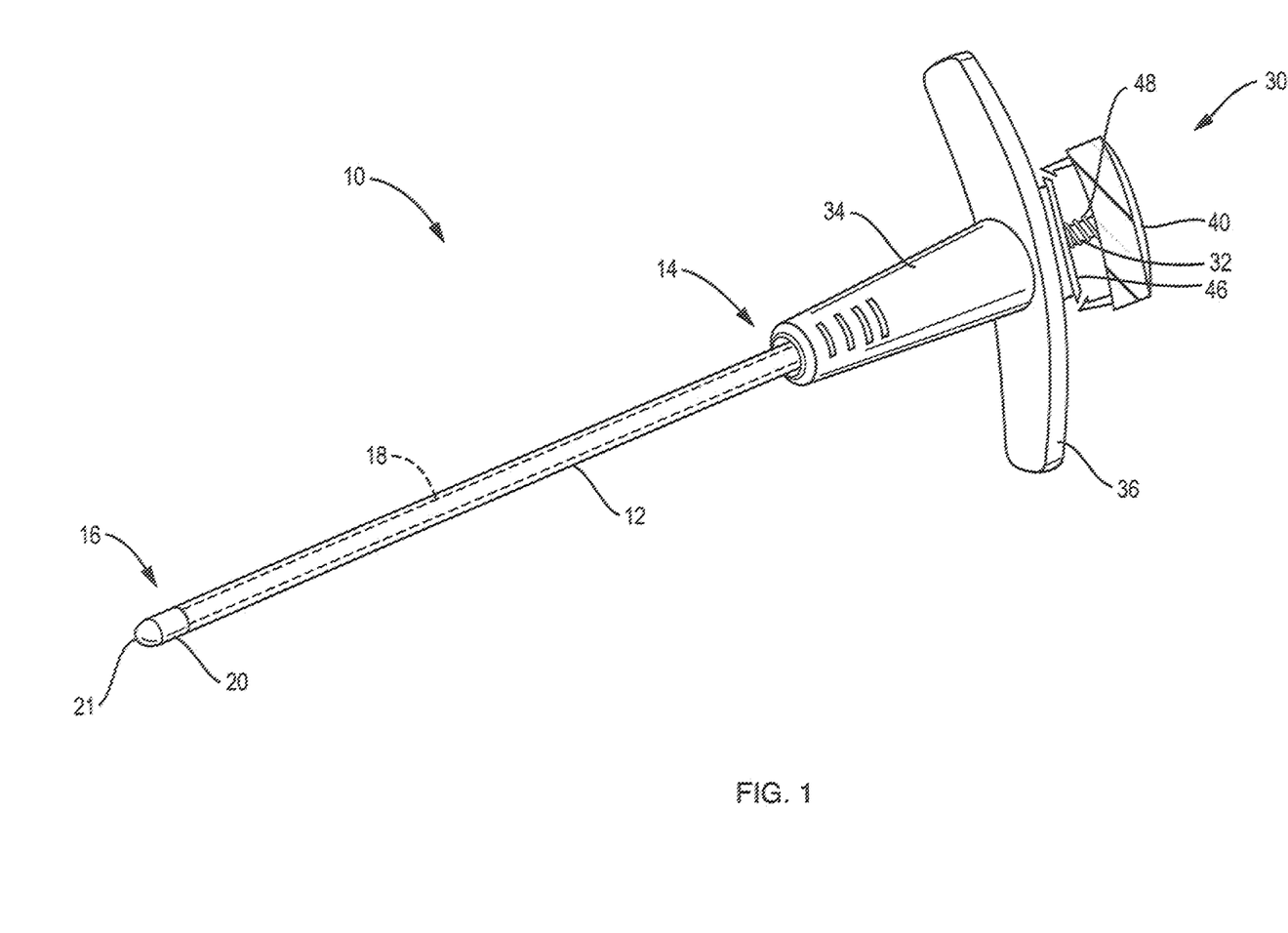
FIG. 1 is a perspective view of a target localizing and marking device according to an embodiment of the invention with the distal end attached.
Figure 2:
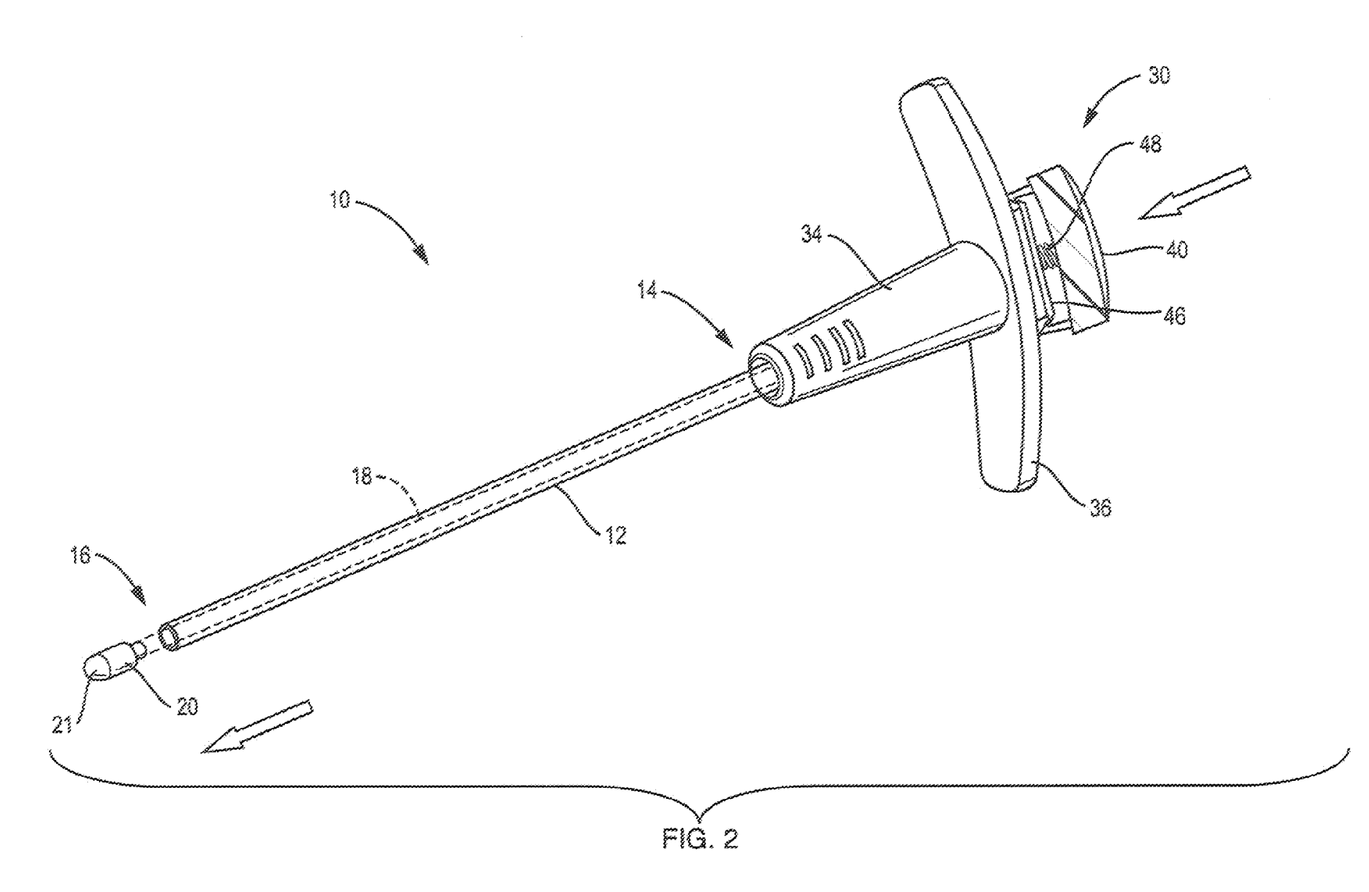
FIG. 2 is a perspective view of the device of FIG. 1 with the distal end deployed.

Referring now to FIGS. 1-2, a target localizing and marking device embodying the present invention is indicated generally by the reference numeral 10. The device 10 is compatible with, and visible (at least in part) by, at least one imaging modality including, but not limited to, magnetic resonance imaging (MRI), x-ray, ultrasound, computed tomography (CT), nuclear medicine and position emission tomography (PET), and is compatible with currently known biopsy localizing and marking techniques. Functionally, the device 10 serves as an obturator for localizing a predetermined target site, such as a biopsy site, and further serves as a marker deployment device capable of selectively delivering a portion of its distal end as a site marker to the target site for future identification. Thus, by serving at least these purposes, the device 10 advantageously eliminates the need to employ separate and distinct devices to localize and mark a target tissue site during a medical procedure, such as a biopsy procedure. However, although the device can serve as both a localizing and marking device, it should be noted that the device may be used entirely as a stand-alone obturator or entirely as a stand-alone marker deployment device if so desired.

The device 10 comprises an elongated body or cannula 12 defining a proximal end 14, a distal end 16, a lumen 18 extending between the proximal and distal ends, and a tip member 20 releasably attached to and forming part of the distal end 16. In FIG. 1, the tip member 20 is shown in its initial state, attached to the cannula 12, so that the device 10 as a whole can be used as an obturator for localizing a target site. In FIG. 2, however, the tip member is shown in its deployed state, separated from the cannula 12 for marking a target site. The tip member 20 provides image enhancing and marking features, which are described in further detail below. Opposite the tip member, a tip member deployment mechanism 30 is disposed on the proximal end of the cannula 12. The deployment mechanism 30 is manually engageable and operable to separate the tip member from the distal end of the cannula and deploy the tip member 20 to a predetermined target site. In one embodiment, the cannula 12 has a generally cylindrical shape with an outer surface generally sized to fit within (and extend through) the inner lumen or working channel 74 of an outer positioning cannula 60 (see, e.g. FIG. 9). However, as recognized by those having ordinary skill in the art, the cannula can take on any of numerous shapes and, therefore, the shape of the cannula should not be construed in a limiting sense. In some embodiments, the cannula 12 is made of a medical grade resin, a polymeric material such as polycarbonate or other MRI compatible material. However, for use with other imaging modalities, the cannula could be made of any of numerous materials that are known to be compatible with the desired imaging modality as recognized by those having ordinary skill in the art.

Figure 3A:
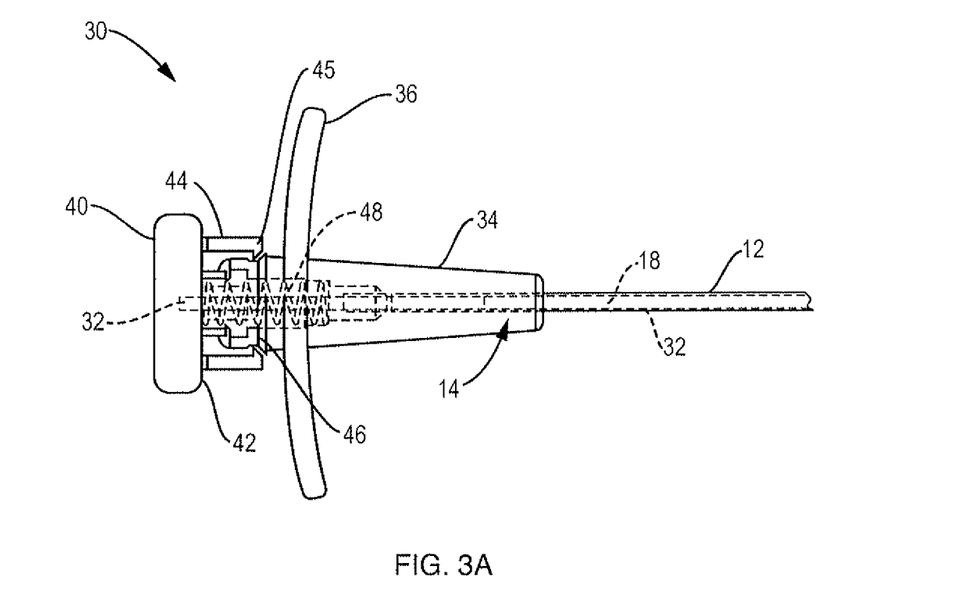
FIG. 3A is a partial side cross-sectional view of the deployment mechanism of the device shown in FIG. 1, where the mechanism is shown in the first position.
Figure 3B:
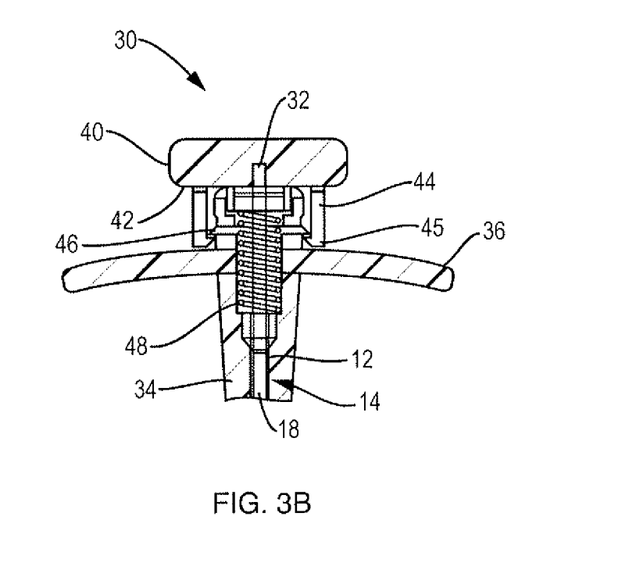
FIG. 3B is a partial side cross-sectional view of the deployment mechanism of the device shown in FIG. 1, where the mechanism is shown in the second position.

Referring now to FIGS. 3A and 3B, the tip member deployment assembly 30 is shown in further detail. In one embodiment, the tip deployment mechanism 30 generally includes a push-rod 32, a hub 34, a handle 36 and a deployment trigger 40. The hub 34 is disposed over the proximal end 14 of the cannula 12 and is fixed relative to the cannula 12 to secure the deployment mechanism 30 to the cannula 12. The push-rod 32 is dimensioned to slidably pass through the hub 34 and into the open proximal end 14 of the cannula 12, and is dimensioned to slidably pass through the lumen 18 of the cannula 12 to the distal end 16 (see, e.g. FIG. 4A). Having this configuration, the push-rod 32 is able to slide axially within the cannula 12 between a retracted position (FIG. 4A) and an extended position (FIG. 4B). In one embodiment, the push-rod 32 is biased toward the retracted position and is adapted to contact the tip member 20 when in the extended position to separate the tip member 20 from the cannula 12 and deploy the tip member 20 to the predetermined target site. Further, the push-rod 32 may have an outer diameter that is substantially contiguous with the lumen of the cannula 12. In this fashion, the push-rod 34 operates to close or block the open distal end 16 of the cannula after the tip member 20 is deployed, which prevents the tip member 20 from inadvertently engaging the cannula 12 and thus being moved away from the target site when the device 10 is removed from the target site.

As noted above, the trigger mechanism 30 includes a deployment trigger 40 attached to the proximal end 14 of the cannula 12. As illustrated in FIGS. 3A-B, the push-rod 32 is attachable to the deployment trigger 40 such that the deployment trigger 40 is operable to advance the push rod toward the distal end 16 of the cannula 12 from the retracted position (FIG. 4A) toward the extended position (FIG. 4B). In one embodiment, the deployment trigger 40 includes at least one retaining arm 44 extending from a first surface 42 of the trigger 40. The at least one retaining arm 44 includes a hook-like engaging member 45, which is adapted to engage a complimentary retaining rim 46 (best shown in FIG. 3A) disposed toward the proximal end of the hub 34. In one embodiment, the trigger 40 is movable from a first position, wherein the at least one engaging member 45 abuts the proximal edge of the retaining rim 46, maintaining the push-rod 32 in the retracted position; and a second position, wherein the at least one engaging member 45 engages the distal edge of the retaining rim 46, maintaining the push-rod 32 at or near the extended position. Hence, the engagement of the at least one engaging member 45 and the retaining rim 46 effectively operates to lock the push-rod 32 in place after the tip member 20 has been separated and released from the cannula 12. This engagement procedure provides a tactile and/or audible indication to the user that the tip member 20 has been deployed. The tactile indication is force feedback from snapping the at least one engaging member 45 onto the retaining rim 46. The audible indication is provided by the user actually hearing a "snapping" or "clicking" sound when the deployment trigger 40 is engaged with the rim 46.

As best illustrated in FIG. 3A, the deployment trigger 40 further includes a biasing member 48, such as a coil spring, disposed between the hub 34 and the deployment trigger 40. The spring 48 concentrically surrounds a proximal end of the push-rod 32, wherein one end of the spring frictionally engages a central portion of the deployment trigger 40 and the opposite end of the spring frictionally engages the hub 34. The spring 48 is adapted to maintain the longitudinal alignment between the deployment trigger 40 and the hub 34. This allows for the push-rod 32 to be substantially stabilized when being axially advanced toward the distal end 16 the cannula 12. Further, the spring 48 biases the deployment trigger 40 toward the first position, which in turn biases the push-rod 32 toward the retracted position. Although the spring 48 is depicted as a coil spring, it should be noted that the spring can take on any of numerous configuration such as, for example, a leaf spring or a torsion spring. Further, if desired, the spring could be replaced by other known biasing members, including but not limited to, elastic or elastomeric biasing members.

As recognized by those of ordinary skill in the art, the above-described deployment mechanism 30 embodies but one way of deploying the tip member 20 relative to the cannula 12. Accordingly, it should be noted that other known mechanisms could be used to deploy the tip member. By way of example, the mechanism 30 could include a pull member (as opposed to a push-rod), such as a pull rod or a pull wire (not shown), disposed within the cannula 12 and movable between an extended position and a retracted position. In this embodiment, the pull member would be releasably coupled to the tip member and adapted to break-away or otherwise separate from the tip member when moved from the extended position toward the retracted position. Hence, when the pull member is in the extended position, the tip member would be coupled to the cannula, and when the tip member is in the retracted position, the tip member would be decoupled from the cannula so as to release the tip member into a target site.

With reference to FIGS. 4A and 4B, the distal end 16 of the device 10 is shown in further detail; more particularly, the distal end is shown with the tip member 20 attached to the cannula 12 (FIG. 4A) and with the tip member 20 released from the cannula 12 (FIG. 4B). In a preferred embodiment, the distal end of the tip member 20 defines a blunt tip 21 configured to penetrate through a pre-formed tissue pathway leading to a target site without piercing and/or cutting tissue. Further, the blunt tip 21 prevents unwanted tissue piercing and/or cutting when the device 10 is manipulated to localize the target tissue site. However, the tip member 20 could define a tissue-piercing tip (not shown), such as a trocar tip, thus enabling the device 10 to perform as a tissue-piercing stylet if so desired.

The tip member 20, which in one aspect is operable as a selectively deployable marker, is generally dimensioned so that its outer diameter D1 approximates the outer diameter D2 of the cannula 12, so that the outer diameter of the complete distal end 16 of the device 10 (i.e. when the tip member 20 is attached to the cannula 12) is consistent along the common longitudinal axis A. However, it is conceivable that the outer diameter of the tip member 20 could exceed the outer diameter of the cannula 12 and vice versa if desired. Moving on, the tip member 20 defines a reduced diameter portion 22 having a diameter D3 slightly greater than the diameter D4 of the cannula lumen 18 (but less than diameters D1 and D2), so that the reduced diameter portion 22 snugly fits within the cannula lumen 18, creating a friction or interference fit therebetween (see FIG. 4A). The friction fit is such that the tip member 20 will remain attached to the cannula 12 (i.e. the reduced diameter portion 22 will remain inside the lumen 18) until the push-rod 32 contacts the tip member 20 and overcomes the frictional forces holding the tip member in place. To further secure the tip member 20 to the cannula, at least one retaining member 50, such as a holding tab, is optionally positioned slightly inboard of the outermost tip 52 of the distal end 16 of the cannula 12. The at least one retaining member 50 is formed on an internal surface 54 of cannula 12 and is sized so as to frictionally engage the reduced diameter portion 22 of the tip member 20. Further, the at least one retaining member 50 is constructed of a suitable material having a predetermined degree of flexibility such that a predetermined amount of force exerted by the tip member 20 upon contact with the push-rod 32 will flex the retaining member 50 out of engagement with the tip member 20. As will be recognized by those having ordinary skill in the art, the tip member 20 can be secured to the distal end 16 of the cannula 12 in many of numerous ways, enabling the tip member 20 to remain attached until acted upon by the push-rod. For example, the tip member 20 could be attached to the cannula 12 via a frangible coupling or by an adhesive adapted to release the tip member 20 when overcome by a predetermined amount of force generated by the push-rod 32.

The tip member 20 further defines an outer shell 24 and at least one inner chamber 26. At least one image enhancing component 28 is disposed on the outer shell 24 of the tip member and/or within the at least one inner chamber. In an exemplary embodiment, the image enhancing component 28 is preferably an MRI compatible and identifiable metallic material, such as Inconel® 625, titanium or other material with similar magnetic characteristics. Alternatively, a liquid contrast agent may be utilized. Suitable liquid contrast agents include polypropylene glycol (PPG), fluro-deoxyglucose (FDG), technicium 99, Gadolinium, and other MRI compatible contrast agents that are currently known or later become known. With the inclusion of the image enhancing component, the tip member 20 provides a reference point on the device 10 in an MRI image (or other suitable imaging modality) relative to a predetermined target site, such as a breast biopsy site. In some embodiments, the tip member 20 and image enhancing component 28 are bioabsorbable and, therefore will degrade and be absorbed by the body after a predetermined time period.

In addition to the image enhancing component, a marking component 29 is also provided. The marking component is typically a permanent site marker configured to remain within a body after the tip member 20 and image enhancing component 28 are absorbed by the body. However, if desired, the marking component could be bioabsorbable and could be configured to degrade at a slower or faster rate relative to the tip member 20 and/or image enhancing component 28. The marking component 29 is housed within the inner chamber 26 of the tip member 20 and is adapted to be visible under multiple imaging modalities, including but not limited to, MRI, x-ray, ultrasound, tomography and nuclear medicine. To enhance visibility and distinguish the marking component from its surroundings during imaging, the marking component 29 may take on a predetermined shape. For example, in the illustrated embodiment the marking component is shaped like a ribbon. In other embodiments (not shown), the marking component is shaped like a bow-tie or the venus symbol. In any case, it should be noted that the marking component 29 could take on any of numerous shapes and, therefore, the shape depicted in the drawings should not be construed in a limiting sense.

Referring now to FIGS. 7-11, a medical procedure using a system 70 employing the target localizing and marking device 10 of the present disclosure will be described. In one embodiment, the system 70 is used to conduct a biopsy of a lesion within a patient's body. The target tissue or lesion to be biopsied and/or removed from the patient's body (denoted generally by mass 80 in FIG. 7) is located under the guidance of a medical imaging system, such as an MRI system or other suitable imaging modality system. A reference structure 82 may be positioned adjacent the patient to assist in locating the target tissue. The location of the target tissue 80 relative to the reference structure 82 may be determined along one or more axis. In the illustrated embodiment, the target tissue location relative to reference structure 82 is determined along the X and Y axes; however, the target tissue location may also be determined along all three of the X, Y and Z axes.

Figure 7:
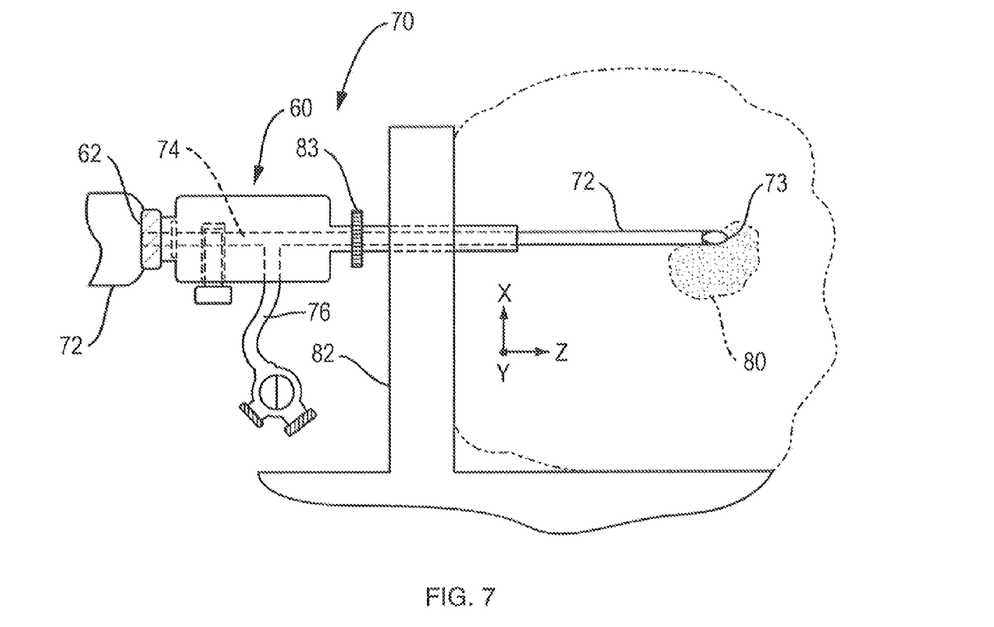
FIGS. 7-12 are elevational views illustrating a medical procedure using the device of FIG. 1 to localize and mark a biopsy site.

In one embodiment, reference structure 82 includes a support grid (not shown) having a number of holes therethrough. Each hole is sized to allow passage of an outer positioning or introducing cannula 60. The hole through which the outer cannula 60 is ultimately inserted is determined by the location of the target tissue 80 relative to the reference structure 82 along the X and Y axes. The patient and reference structure 82 are viewed using a medical imaging system, such as MRI, to determine the location of the target tissue relative to reference structure 82.

Figure 8:
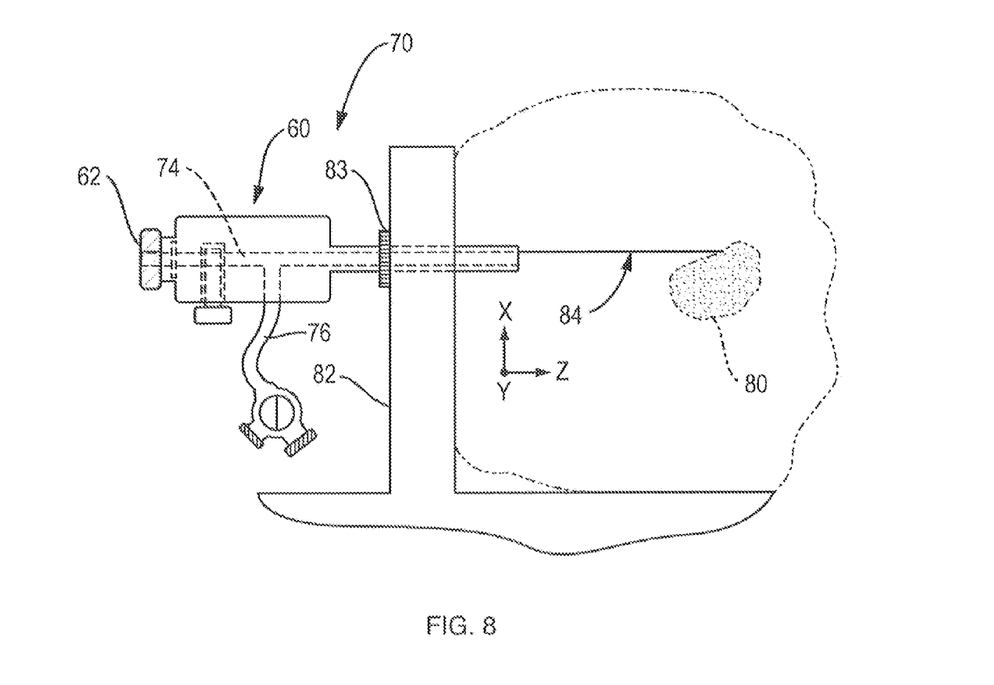

With particular reference to FIGS. 7-8, after application of anesthesia, an introducer stylet 72 having a tissue piercing tip 73 (such as a trocar tip) and a portion of the outer cannula 60 are inserted through the support 82 and into the patient's body, creating a pathway 84 leading to the target tissue site 80. In one embodiment, outer cannula 60 is sized to permit only a single instrument therewithin at a time. Thus, the introducer stylet 72 is removed from the patient's body after creating the pathway, leaving behind the outer cannula 60 (see, e.g. FIG. 8).

Fluids may be inserted into or removed from the patient's body through an inner lumen 74 in the outer cannula 60 via a fluid conduit 76. These fluids may include, for example, additional anesthetics and/or saline solution to cleanse pathway 84 and remove blood. Accumulated blood and other fluids within the pathway 84 may be aspirated through the fluid conduit 76 or by inserting an aspirating wand 98 (FIG. 11) prior to insertion of the device 10.

Figure 9:
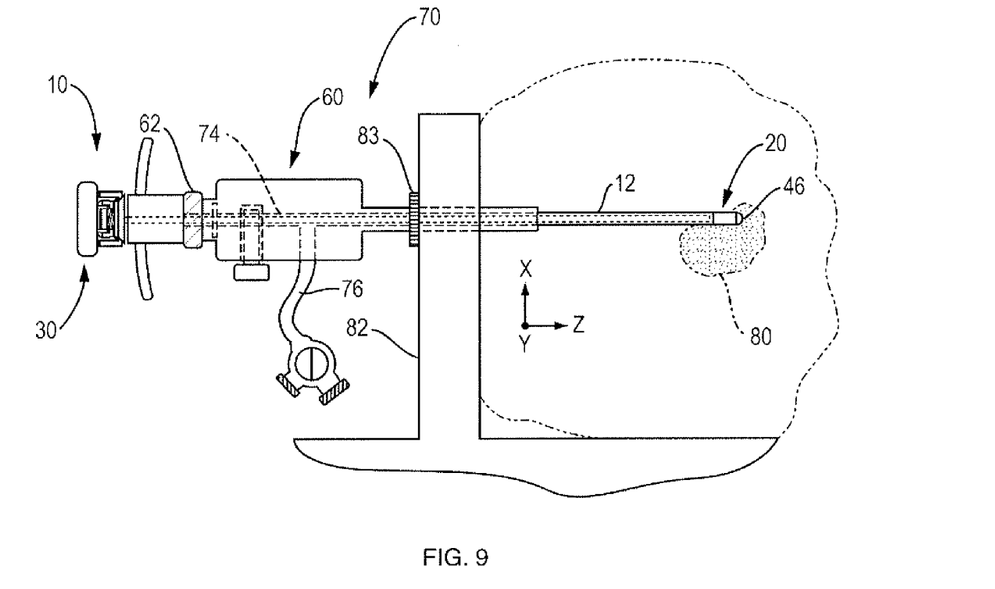

Drawing attention to FIG. 9, once the introducer stylet 72 is removed from the outer cannula 60, the localizing and marking device 10 may be inserted into the patient's body through the outer cannula 60 and into the pathway 84. With the device 10 properly inserted into the outer cannula 60, an image of the target site 80 is again taken to determine the location of the target site 80 relative to the distal portion of the device 10 and/or reference structure 82. If the target site 80 is in the desired position along the Z-axis, the device 10 is removed from the outer cannula 60. However, if the target site 80 is not in the desired position, then the position of the device 10 and the outer cannula 60 is modified along the Z-axis until the desired position is of the site 80 is localized (i.e. confirmed and achieved) prior to inserting the biopsy device 90.

Figure 10:
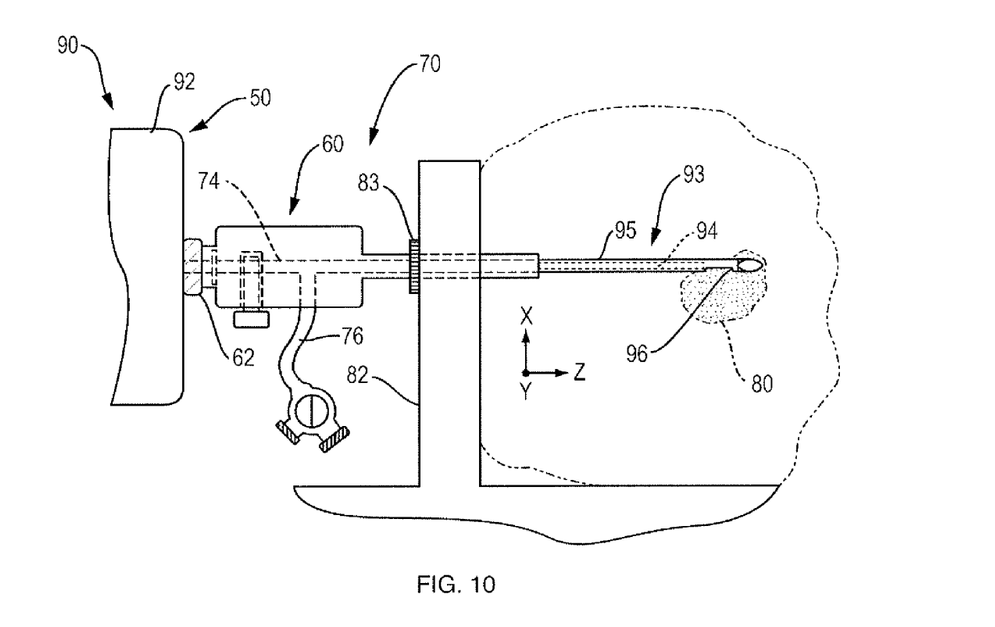

Once the desired position is achieved, a depth limiting member 83 is moved against reference structure 82 to inhibit movement of outer cannula 60 further into the patient. When no reference structure 82 is used, the depth limiting member may be moved directly against the patient's skin. Referring now to FIG. 10, the device 10 is then removed from the outer cannula 60 and a biopsy device 90 is inserted into the outer cannula 60 until the device 90 abuts the proximal end 62 of the outer cannula 60. The biopsy device 90 typically includes a hand piece 92 and a cutting element 93 including an outer cannula 94 defining a tissue receiving opening and, a cutting cannula 95. In the illustrated embodiment, one or more samples of target tissue 80 are removed from the patient through the tissue-receiving opening 96.

Figure 11:
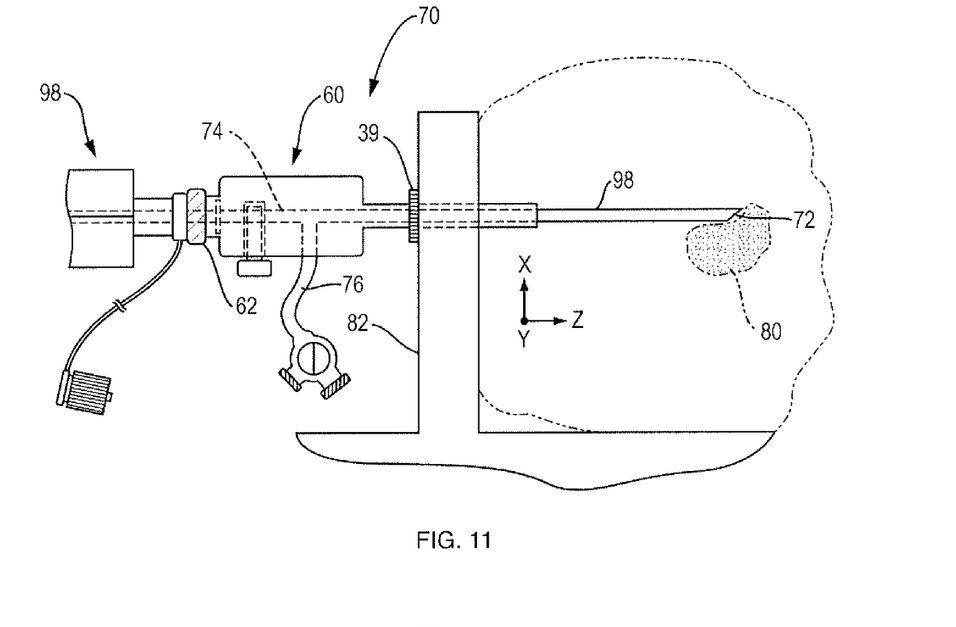
Figure 12:
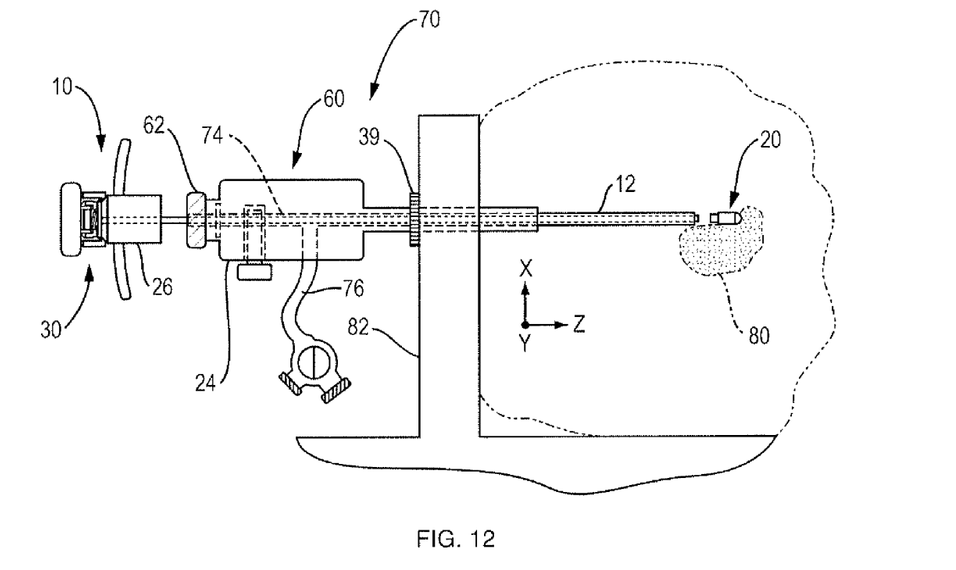

After completion of the biopsy, the biopsy site can be aspirated if so desired using an aspirating wand 98 (see, e.g. FIG. 11). During or after aspiration, a final image of the biopsy site can be taken to confirm removal of the target tissue. With reference to FIG. 12, after the image is taken, the device 10 is then reinserted into the outer cannula 60 and positioned such that the tip member 20 is located within the biopsy site (as illustrated in FIG. 9). The deployment mechanism 30 is then engaged to separate the tip member 20 from the device (i.e. from the distal end of the cannula 12) and deploy the tip member 20 into the biopsy site 80 to mark the site for future identification.

Figure 5:
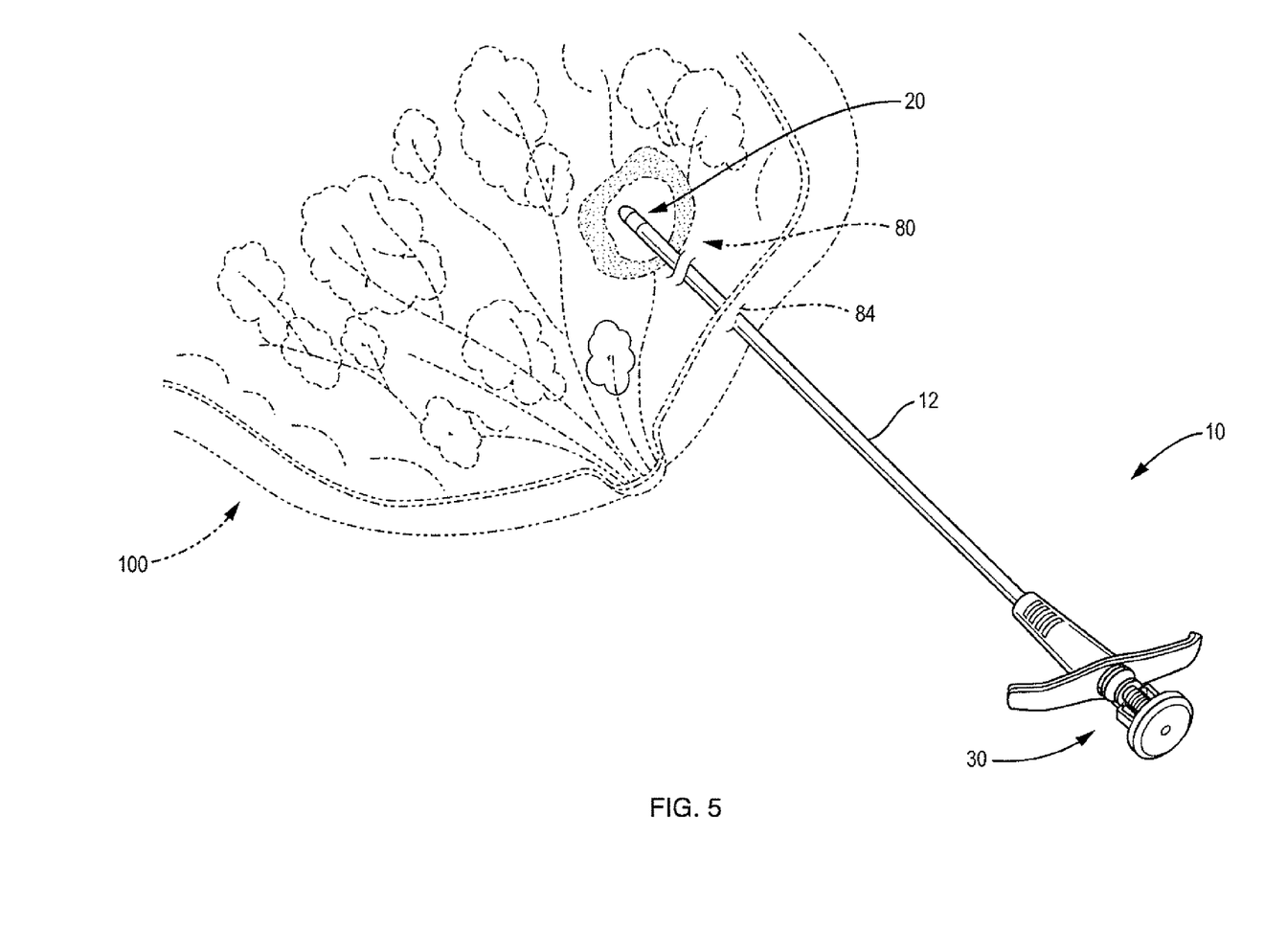
FIG. 5 is a perspective view of a biopsy site in a human breast showing the breast in section and the device of FIG. 1 inserted into the breast to localize the target site.
Figure 6:
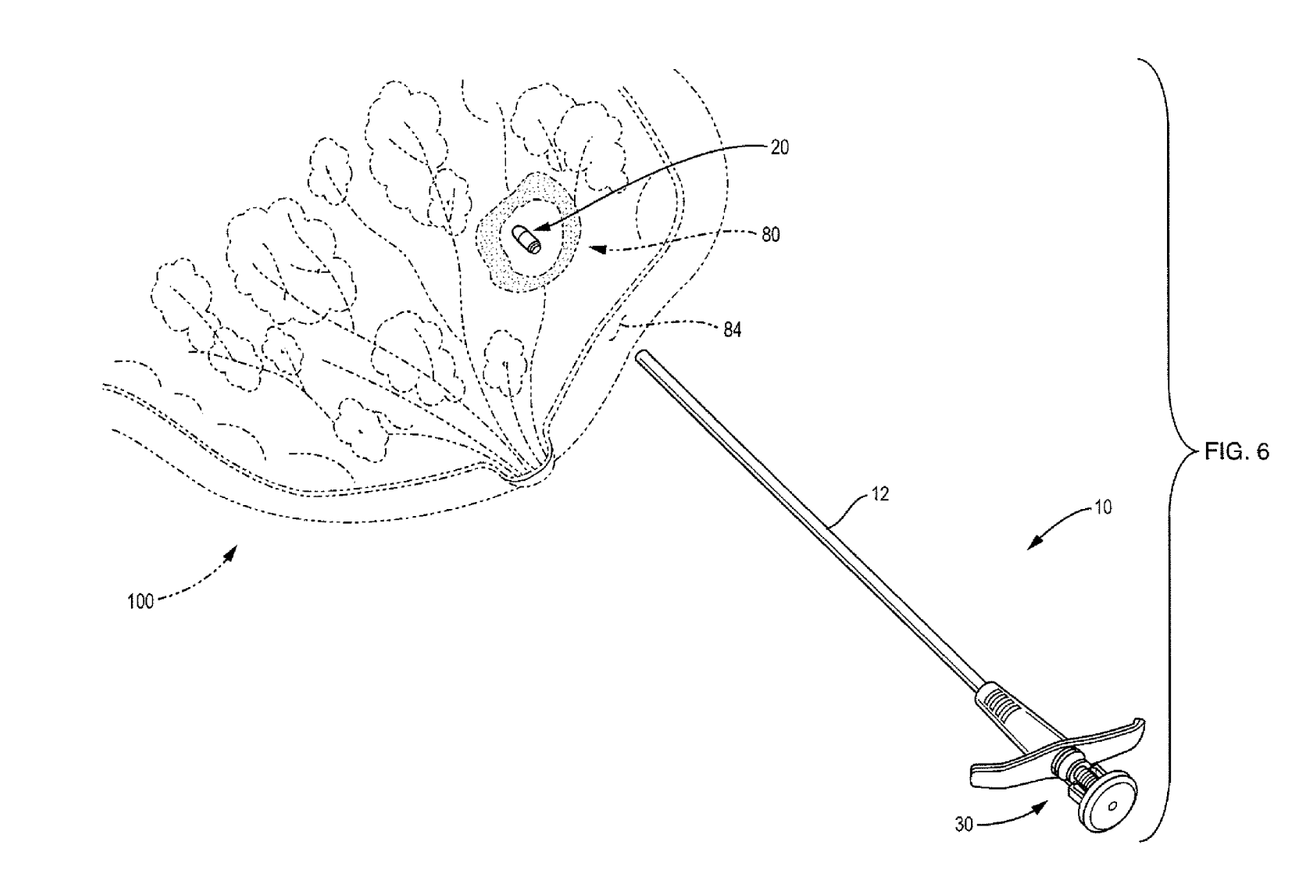
FIG. 6 is a perspective view of a biopsy site in a human breast showing the breast in section and the distal end of the device of FIG. 1 deployed into the breast to mark the target site.

While the above procedure employs a reference structure 82 to locate the target tissue, the reference structure is not necessarily required and a more "free-hand" approach (depicted in part in FIGS. 5-6) may be undertaken. For example, in a breast biopsy procedure, before the biopsy is performed, the device 10 can be inserted by hand through a tissue pathway 84 in the breast 100 (created by an introducer stylet or otherwise) to a target tissue or biopsy site 80, as illustrated in FIG. 5. Once inserted, the breast 100 and inserted device 10 are imaged to identify and localize the site 80. After the biopsy is performed, the device 10 is then reinserted by hand into the site 80 and the tip member 20 is deployed to mark the site for future identification, as illustrated in FIG. 6.

The present disclosure has been particularly shown and described with reference to the foregoing embodiments, which are merely illustrative out of the disclosure. It should be understood by those having ordinary skill in the art that various alternatives to the embodiments of the disclosure described herein may be employed in practicing the disclosure without departing from the spirit and scope of the disclosure as defined in the following claims.

It is intended that the following claims define the scope of the invention and that the method and apparatus within the scope of these claims and their equivalents be covered thereby. This description of the disclosure should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A medical target localizing and marking device, comprising:

a cannula defining a proximal end, a distal end and a lumen extending between the proximal and distal ends;

a tip member releasably attached to and forming part of the distal end of the cannula, the tip member defining an outer shell and a plurality of inner chambers;

an image enhancing component disposed in a first inner chamber of the plurality;

a marking component disposed in a second inner chamber of the plurality; and a tip member deployment mechanism including a manually engageable actuator, a portion of which is dimensioned to slidably pass through the lumen of the cannula, the deployment mechanism selectively operable to separate the tip member from the distal end of the cannula and deploy the tip member to a predetermined target site.

2. The device of claim 1, wherein the device is magnetic resonance imaging compatible.

3. The device of claim 1, wherein the deployment mechanism includes a push rod slidably disposed within the cannula and movable between a retracted position and an extended position, wherein the push rod is biased toward the retracted position, and wherein the push rod is adapted to contact the tip member when the push rod is in the extended position to separate the tip member from the cannula and deploy the tip member to the predetermined target site.

4. The device of claim 3, wherein the cannula includes at least one retaining member adapted to secure the tip member to the cannula when the push rod is in the retracted position and release the tip member when the push rod is in the extended position.

5. The device of claim 4, wherein the at least one retaining member is a holding tab connected to an internal surface of the cannula adjacent to the distal end of the cannula, the holding tab frictionally engaging at least a portion of the tip member, and the push rod configured to overcome the frictional engagement to deploy the tip member.

6. The device of claim 1, wherein the tip member and image enhancing component are bioabsorbable.

7. The device of claim 1, wherein the marking component is a solid component detectable under multiple imaging modalities.

8. The device of claim 1, wherein the marking component has a predetermined shape.

9. The device of claim 8, wherein the predetermined shape is one of a venus symbol, bow-tie, and ribbon.

10. The device of claim 1, wherein the image enhancing component is compatible with magnetic resonance imaging and detectable under magnetic resonance imaging.

11. The device of claim 10, wherein the image enhancing component is at least one of a metallic material and a liquid contrast agent.

* * * * *